US009339277B2

(12) United States Patent  (10) Patent No.: US 9,339,277 B2
Jansen et al.  (45) Date of Patent: May 17, 2016

(54) COMPUTER-ASSISTED HIP REPLACEMENT SURGERY

(75) Inventors: Herbert André Jansen, Montréal (CA); Louis-Philippe Amiot, Hampstead (CA); Isabelle Fontaine, Montréal (CA); Sébastien Jutras, Montréal (CA); Daniel Odermatt, Montréal (CA); Benoît Pelletier, Montréal (CA)

(73) Assignee: ORTHOSOFT HOLDINGS INC., Montreal, Quebec (CA)

( * ) Notice: Subject to any disclaimer, the term of this patent is extended or adjusted under 35 U.S.C. 154(b) by 2692 days.

(21) Appl. No.: 10/677,432

(22) Filed: Oct. 3, 2003

(65) Prior Publication Data

US 2004/0230199 A1   Nov. 18, 2004

Related U.S. Application Data

(60) Provisional application No. 60/415,809, filed on Oct. 4, 2002, provisional application No. 60/465,805, filed on Apr. 28, 2003.

(51) Int. Cl.
*A61B 19/00*     (2006.01)
*A61B 17/16*     (2006.01)
(Continued)

(52) U.S. Cl.
CPC .............. *A61B 17/1666* (2013.01); *A61B 5/064* (2013.01); *A61B 5/103* (2013.01);
(Continued)

(58) Field of Classification Search
USPC ........................... 623/22.12, 908; 606/89, 102
See application file for complete search history.

(56) References Cited

U.S. PATENT DOCUMENTS 4,519,100 A   5/1985   Wills et al.
5,037,424 A   8/1991   Aboczsky
(Continued)

FOREIGN PATENT DOCUMENTS

WO   WO-99/59487        11/1999
WO   WO-01/67979 A1     9/2001
WO   WO 02/062250       8/2002

*Primary Examiner* — Thomas J Sweet
*Assistant Examiner* — Megan Wolf
(74) *Attorney, Agent, or Firm* — Norton Rose Fulbright Canada LLP

(57) ABSTRACT

A CAS system and method for guiding an operator in inserting a femoral implant in a femur as a function of a limb length and orientation of the femoral implant with respect to the femur, comprising a reference tool for the femur, a registration tool, a bone altering tool and a sensing apparatus. A controller is connected to the sensing apparatus to: i) register a frame of reference of the femur by calculating surface information provided by the registration tool as a function of the position and orientation of the registration tool provided by the sensing apparatus, and/or retrieving in a database a model of the femur; ii) calculate a desired implant position with respect to the frame of reference as a function of the limb length; and iii) calculate a current implant position and orientation in relation to the desired implant position with respect to alterations being performed in the femur with the bone altering tool, as a function of the position and orientation of the bone altering tool provided by the sensing apparatus and of a digital model of a femoral implant provided by the database. The database is connected to the controller for the controller to store and retrieve information relating to an operation of the controller. The computer-assisted system may be used to guide an operator in inserting a pelvic implant in an acetabulum as a function of an orientation of the pelvic implant with respect to the pelvis.

10 Claims, 7 Drawing Sheets

(51) Int. Cl.

| | | |
|---|---|---|
| *A61B 5/06* | (2006.01) | |
| *A61B 5/103* | (2006.01) | |
| *A61B 17/15* | (2006.01) | |
| *A61B 17/17* | (2006.01) | |
| *G09B 23/28* | (2006.01) | |
| *G09B 23/30* | (2006.01) | |
| *A61B 5/00* | (2006.01) | |
| *A61F 2/34* | (2006.01) | |
| *A61F 2/46* | (2006.01) | |
| *A61F 2/30* | (2006.01) | |
| *A61F 2/36* | (2006.01) | |

(52) U.S. Cl.
CPC ............ *A61B 17/15* (2013.01); *A61B 17/1703* (2013.01); *A61B 17/175* (2013.01); *A61B 17/1717* (2013.01); *A61B 17/1746* (2013.01); *A61B 90/36* (2016.02); *A61F 2/4657* (2013.01); *G09B 23/28* (2013.01); *G09B 23/30* (2013.01); *A61B 5/4528* (2013.01); *A61B 5/6878* (2013.01); *A61B 17/1735* (2013.01); *A61B 2034/102* (2016.02); *A61B 2034/2055* (2016.02); *A61B 2034/2068* (2016.02); *A61B 2034/2072* (2016.02); *A61B 2034/256* (2016.02); *A61B 2090/363* (2016.02); *A61B 2090/3983* (2016.02); *A61F 2/34* (2013.01); *A61F 2/4607* (2013.01); *A61F 2/4609* (2013.01); *A61F 2002/30952* (2013.01); *A61F 2002/3611* (2013.01); *A61F 2002/4632* (2013.01); *A61F 2002/4658* (2013.01); *A61F 2002/4668* (2013.01); *A61F 2002/4681* (2013.01); *A61F 2002/4697* (2013.01)

(56) References Cited

U.S. PATENT DOCUMENTS

| | | | |
|---|---|---|---|
| 5,171,248 | A | 12/1992 | Ellis |
| 5,269,785 | A | 12/1993 | Bonutti |
| 5,385,566 | A | 1/1995 | Ullmark |
| 5,628,315 | A | 5/1997 | Vilsmeier et al. |
| 5,643,268 | A | 7/1997 | Vilsmeier et al. |
| 5,682,886 | A | 11/1997 | Wong et al. |
| 5,702,406 | A | 12/1997 | Vilsmeier et al. |
| 5,769,861 | A | 6/1998 | Vilsmeier |
| 5,806,518 | A | 9/1998 | Mittelstadt |
| 5,858,020 | A | 1/1999 | Emery et al. |
| 5,880,976 | A | 3/1999 | Di Gioa, III et al. |
| 5,889,834 | A | 3/1999 | Vilsmeier et al. |
| 5,995,738 | A | 11/1999 | Di Gioa, III et al. |
| 6,002,859 | A | 12/1999 | Di Gioa, III et al. |
| 6,178,345 | B1 | 1/2001 | Vilsmeier et al. |
| 6,205,411 | B1 | 3/2001 | Di Gioa, III et al. |
| 6,214,014 | B1 | 4/2001 | McGann |
| 6,223,067 | B1 | 4/2001 | Vilsmeier et al. |
| 6,351,659 | B1 | 2/2002 | Vilsmeier |
| 6,358,253 | B1 | 3/2002 | Miniaci et al. |
| 6,609,022 | B2 | 8/2003 | Vilsmeier et al. |
| 2002/0198451 | A1* | 12/2002 | Carson .................. 600/424 |
| 2004/0087852 | A1* | 5/2004 | Chen et al. .................. 600/407 |
| 2005/0203384 | A1* | 9/2005 | Sati et al. .................. 600/426 |

* cited by examiner

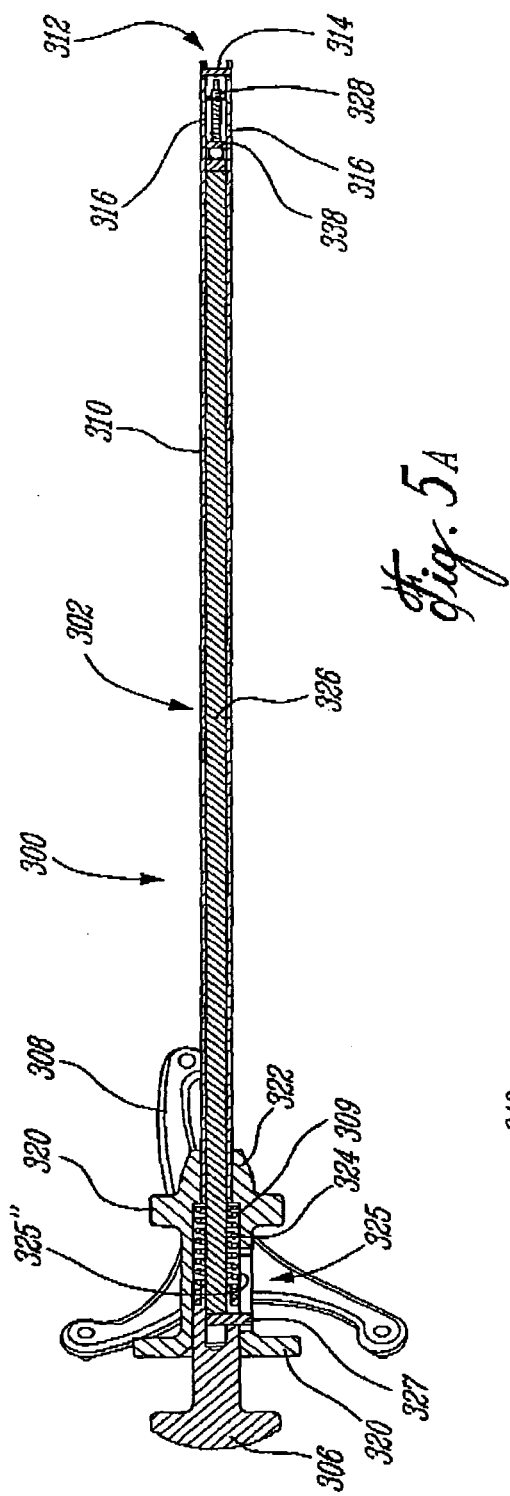
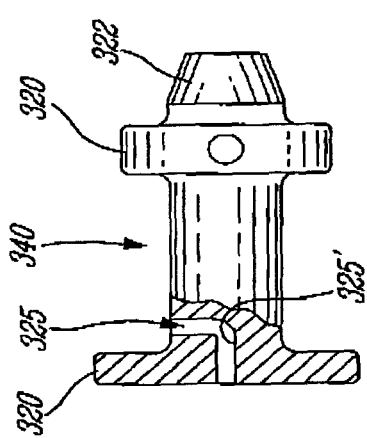
Fig. 5A
Fig. 5B

COMPUTER-ASSISTED HIP REPLACEMENT SURGERY

CROSS-REFERENCE TO RELATED APPLICATIONS

This application claims priority on U.S. Patent Application Ser. No. 60/415,809, filed on Oct. 4, 2002 by the present Applicants, the subject matter of which is incorporated herein by reference. This application also claims priority on U.S. Patent Application Ser. No. 60/465,805, filed on Apr. 28, 2003 by the present Applicants, the subject matter of which is incorporated herein by reference.

FIELD OF THE INVENTION

The present invention generally relates to computer-assisted hip replacement surgery and, more precisely, to hip replacement surgery with minimal preoperative procedures.

BACKGROUND OF THE INVENTION

Total hip replacement surgery involves the introduction of an artificial hip joint in a patient. The artificial hip joint typically consists of a pelvic implant and a femoral implant. The pelvic implant is a cup received in the acetabulum. The femoral implant consists of a spherical portion received at an end of a longitudinal implant portion. The longitudinal implant portion is introduced into the intramedullary canal of the resected femur, with the spherical portion being generally centered with respect to the previous position of the femoral head. Therefore, the femoral head (i.e., spherical portion of the femoral implant) and the cup (i.e., pelvic implant) coact to create the artificial hip joint.

Different output values are of concern in hip replacement surgery. In order to reproduce a natural and/or improved gait and range of motion to a patient, the position and orientation of the implants, the offset of the femur and the limb length must be considered during surgery. The work of the surgeon during hip replacement surgery will have a direct effect on these output values.

Known computer-aided hip replacement surgery techniques presently involve preoperative computerized tomography (CT) steps that enable acquisition of data related to the skeletal configuration of the patient. This data is used, for instance, to determine implant size and to guide the surgeon intraoperatively into reproducing the ideal output values mentioned above.

There are inconveniences to the use of CT. Firstly, it is desired to reduce preoperative steps to a minimum. Ideally, hip replacement surgery would be free of preoperative steps, as this would be logistically preferred. Cost saving issues are involved in the logistic simplification of hip replacement surgery. Moreover, CT uses X-rays, which are known to be hazardous to health.

Accordingly, it is believed that computer-aided hip replacement surgery techniques having minimal preoperative steps would be of great appeal to surgeons and to management of health institutions.

SUMMARY OF THE INVENTION

It is an aim of the present invention to provide a novel method for guiding an operator in inserting implants in hip joint replacement with computer assistance.

It is a further aim of the present invention to provide a method of performing hip joint replacement with minimal preoperative procedures.

It is a still further aim of the present invention to provide a computer-assisted surgery system for guiding an operator in inserting implants in hip joint replacement.

It is a still further aim of the present invention to provide an apparatus for digitizing a center of a bone canal.

Therefore, in accordance with the present invention, there is provided a method of doing surgical treatment with a position tracking system in computer-assisted surgery for guiding an operator in inserting a femoral implant of a hip joint implant in a femur as a function of a limb length and orientation of the femoral implant, comprising the steps of: obtaining a frame of reference of the femur, the frame of reference being trackable in space for position and orientation; providing a digital model of a femoral implant; calculating a desired implant position for the femoral implant with respect to the frame of reference of the femur, as a function of the limb length; and guiding an operator in altering the femur for a subsequent insertion of the femoral implant in the femur by providing information about a current implant position and orientation with respect to the desired implant position, the current implant position and orientation being calculated as a function of the digital model of the femoral implant and of a real-time tracking for position and orientation of at least one surgical tool altering the femur for receiving the femoral implant.

Further in accordance with the present invention, there is provided a method of doing surgical treatment in computer-assisted surgery for guiding an operator in inserting a pelvic implant of a hip joint implant in an acetabulum of a pelvis as a function of a position and orientation of the pelvic implant with respect to the pelvis, comprising the steps of: creating a frame of reference of a pelvis by registering points on the pelvis, the frame of reference being trackable in space for position and orientation; creating a digital model of a surface of an exposed acetabulum of the pelvis by registering points on the surface of the acetabulum as a function of the frame of reference; providing a digital model of a pelvic implant; calculating an initial center of rotation of the acetabulum as a function of the digital model of the surface of the acetabulum; and guiding an operator in altering the acetabulum for a subsequent insertion of the pelvic implant in the acetabulum by providing information about a current implant position and orientation with respect to the initial center of rotation of the acetabulum and the frame of reference, the current implant position and orientation being calculated as a function of the digital model of the pelvic implant and of a real-time tracking for position and orientation of at least one surgical tool altering the acetabulum for receiving the pelvic implant.

Still further in accordance with the present invention, there is provided a method for digitizing an intramedullary canal axis of a bone in computer-assisted surgery, comprising the steps of: performing an opening in a bone to expose an intramedullary canal of the bone; providing a tool trackable in space for position and orientation and a frame of reference on the bone, said tool having a leading end thereof being positionable in a determined way with respect to a surface of the intramedullary canal; and obtaining the axis of the intramedullary canal with respect to the frame of reference by calculating and relating reference points in the intramedullary canal by inserting the leading end of the tool at given depths in the intramedullary canal and calculating a reference point of the intramedullary canal for each said given depths as a function of a position and orientation of said tool having the leading end positioned in said determined way.

Still further in accordance with the present invention, there is provided an apparatus for obtaining an axis of an intramedullary canal of an exposed bone with a position tracking system in computer-assisted surgery, comprising: a detectable device trackable in space for position and orientation; a stem portion secured to the detectable device so as to be tracked for position and orientation, the stem portion having a leading end insertable in an intramedullary canal of the bone through an opening in the bone, and being adapted to be handled by a following end thereof; and a tip portion at the leading end of the stem portion, the tip portion being positionable in a determined way with respect to a surface of the intramedullary canal, such that reference points with respect to the intramedullary canal are calculable as a function of the position and orientation of the detectable device, said reference points being related to define an axis of the intramedullary canal.

Still further in accordance with the present invention, there is provided a computer-assisted surgery system for guiding an operator in inserting a femoral implant of a hip joint implant in a femur as a function of a limb length and orientation of the femoral implant with respect to the femur, comprising: a reference tool securable to the femur and trackable in space for position and orientation; a registration tool trackable in space for position and orientation and handled by the operator to register surface information; a bone altering tool trackable in space for position and orientation; a sensing apparatus, for tracking any one of the tools for position and orientation; a controller connected to the sensing apparatus, the controller being provided to: i) register a frame of reference of the femur by at least one of calculating surface information provided by the registration tool as a function of the position and orientation of the registration tool provided by the sensing apparatus, and retrieving in a database a model of the femur; ii) calculate a desired implant position with respect to the frame of reference as a function of the limb length; and iii) calculate a current implant position and orientation in relation to the desired implant position with respect to alterations being performed in the femur with the bone altering tool, as a function of the position and orientation of the bone altering tool provided by the sensing apparatus and of a digital model of a femoral implant provided by the database; and the database connected to the controller for the controller to store and retrieve information relating to an operation of the controller.

Still further in accordance with the present invention, there is provided a computer-assisted surgery system for guiding an operator in inserting a pelvic implant of a hip joint implant in an acetabulum as a function of an orientation of the pelvic implant with respect to the pelvis, comprising: a reference tool securable to the femur and trackable in space for position and orientation; a registration tool trackable in space for position and orientation and handled by the operator to register surface information; a bone altering tool trackable in space for position and orientation; a sensing apparatus, for tracking any one of the tools for position and orientation; a controller connected to the sensing apparatus, the controller being provided to: i) register a frame of reference of the pelvis by calculating surface information provided by the registration tool as a function of the position and orientation of the registration tool provided by the sensing apparatus; ii) register a digital model of a surface of an exposed acetabulum of the pelvis with respect to the frame of reference by calculating surface information provided by the registration tool as a function of the position and orientation of the registration tool provided by the sensing apparatus; iii) calculate an initial center of rotation of the acetabulum as a function of the digital model; and iv) calculate a current implant position and orientation in relation to the initial center of rotation of the acetabulum and the frame of reference with respect to alterations being performed in the acetabulum with the bone altering tool, as a function of the position and orientation of the bone altering tool provided by the sensing apparatus and of a digital model of an acetabular implant provided by the database; and the database connected to the controller for the controller to store and retrieve information relating to an operation of the controller.

BRIEF DESCRIPTION OF THE DRAWINGS

These and other features, aspects and advantages of the present invention will become better understood with regard to the following description and accompanying drawings wherein:

FIG. 5A is a longitudinal cross-section view of the canal digitizer;

FIG. 5B is a side elevation view of a handle portion of the canal digitizer;

DESCRIPTION OF THE PREFERRED EMBODIMENT

Figure 1:
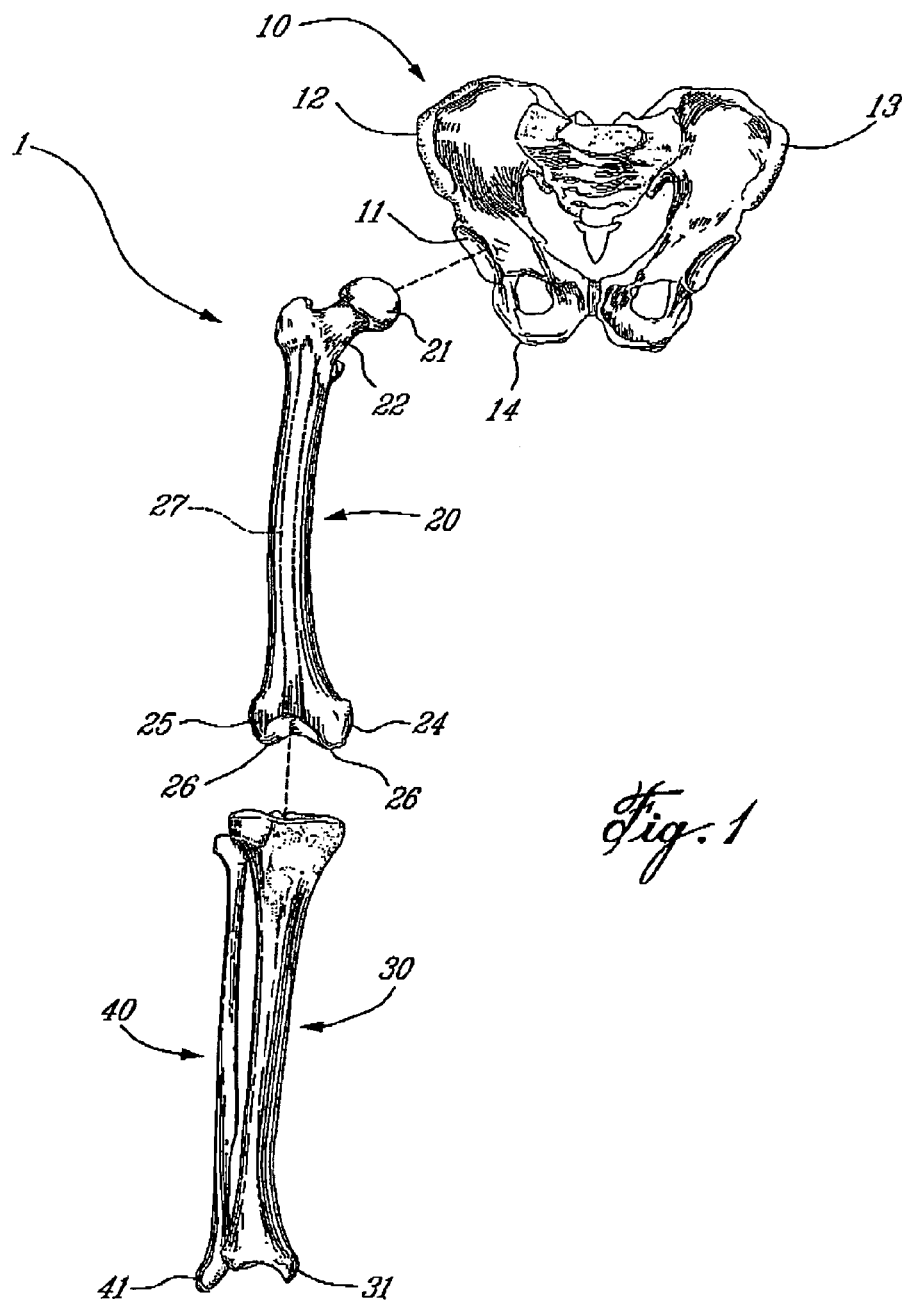
FIG. 1 is a front elevation view of leg bones involved in a hip replacement method in accordance with the present invention.

According to the drawings, and more particularly to FIG. 1, bones of the leg that will be involved in the hip replacement surgery of the present invention are generally shown at 1. FIG. 1 is provided as reference for the description of the steps of the hip replacement surgery method described herein. The bones are the pelvis 10, the femur 20, the tibia 30 and the fibula 40. Hereinafter, parts of these bones will each be referenced by numerals from the same numeric decade. For instance, parts of the pelvis (e.g., the acetabulum 11) will bear reference numerals between 11 and 19.

Figure 2:
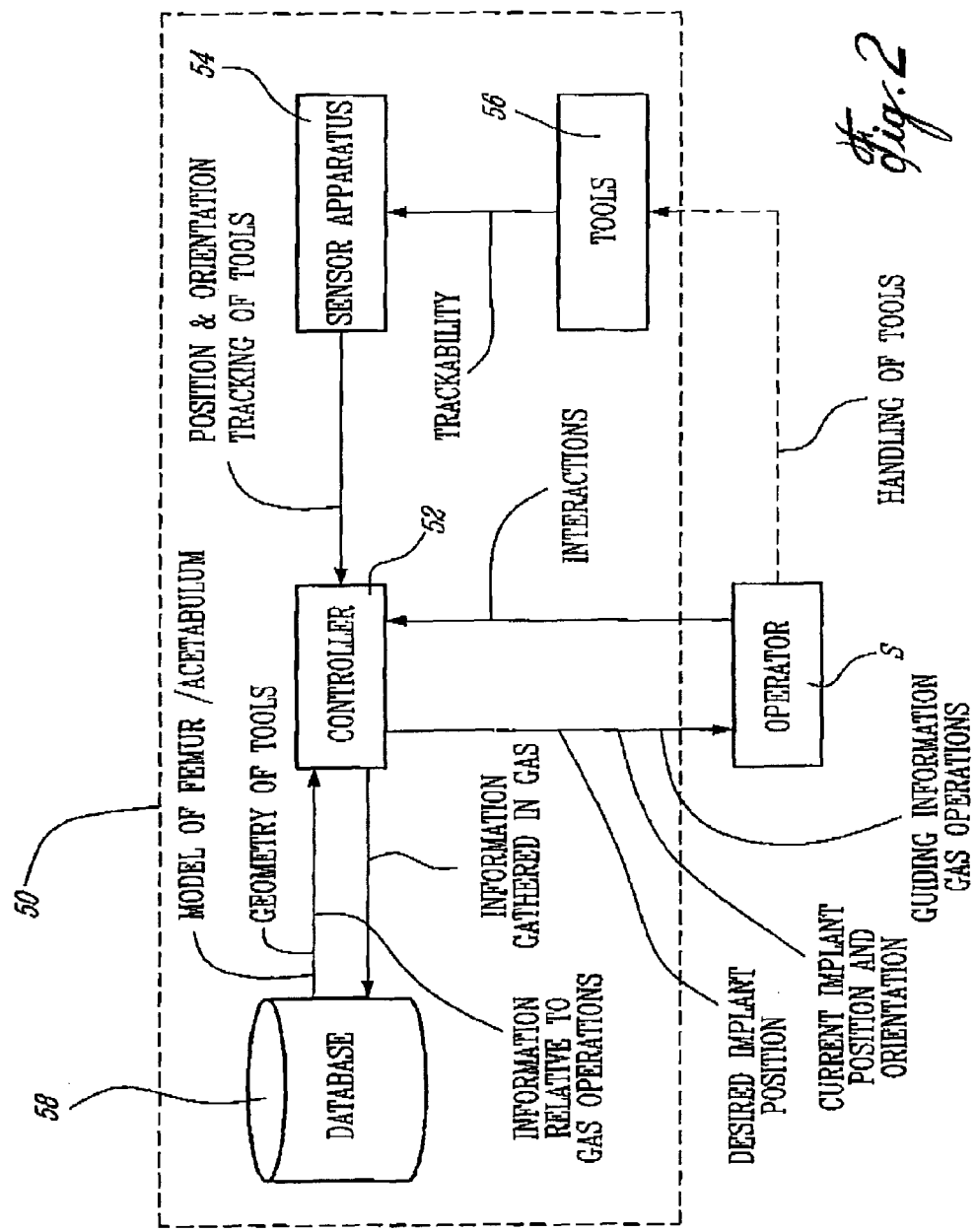
FIG. 2 is a block diagram of a computer-assisted surgery system in accordance with the present invention.

Referring to FIG. 2, a computer-assisted surgery system is generally shown at 50 (hereinafter CAS system 50) and generally consists of a CAS controller 52 connected to sensor apparatus 54. The sensor apparatus 54 tracks for position and orientation tools 56, to be described in detail with the description of the hip replacement surgery method of the present invention. The controller 52 is typically a PC unit that has user interfaces by which a surgeon will receive or send information that will guide him during the hip replacement surgery. For instance, monitors, keyboard, mouse, and foot pedals are a few of the user interfaces that can be provided with the controller 52. A database of the controller 52 is illustrated separately as database 58, and is typically the hard disk drive of the controller 52. A discussion of the preferred system configuration will follow the description of the method 100.

Figure 3:
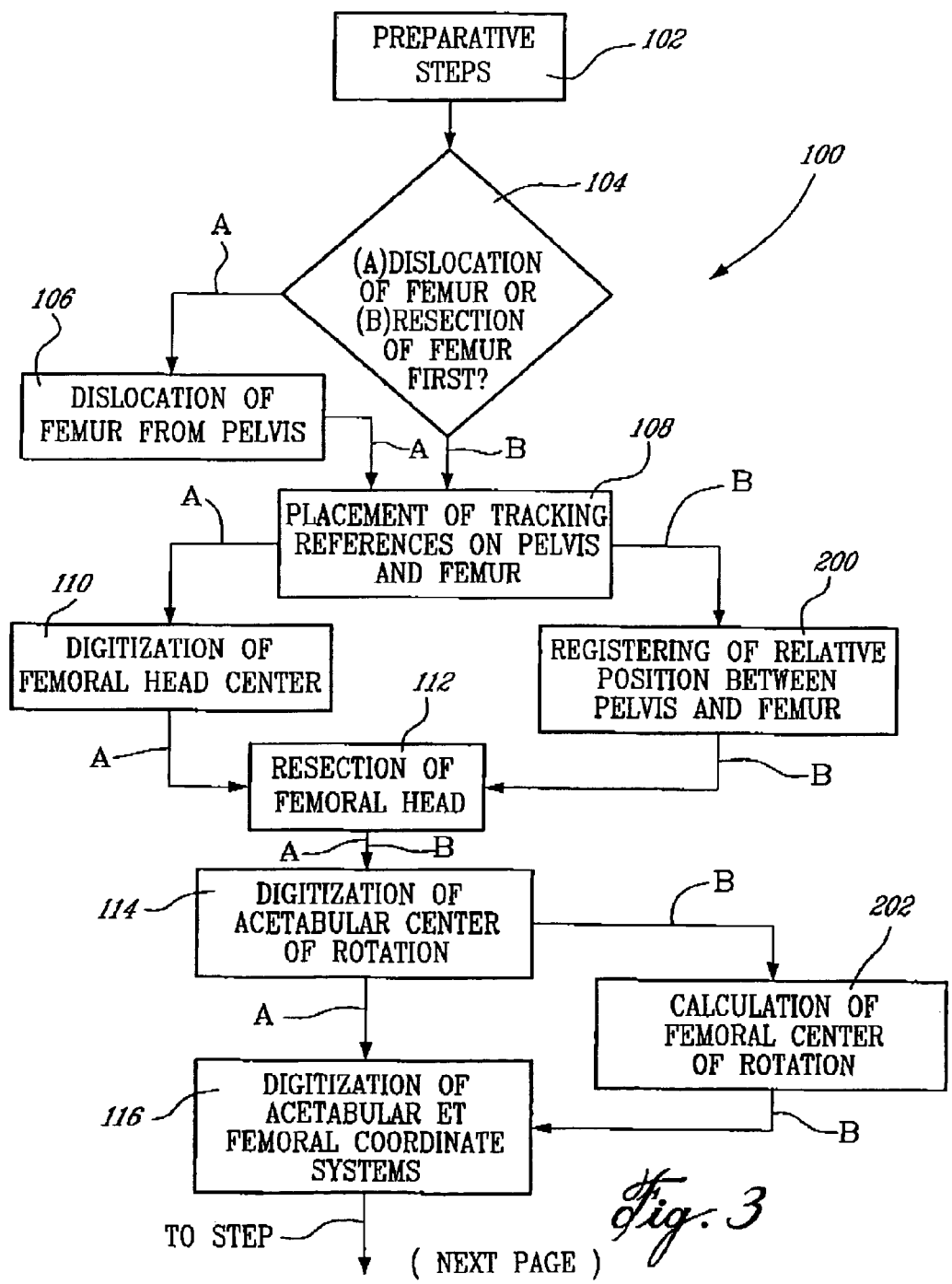
FIG. 3 is a flow chart of a method of hip replacement surgery in accordance with the present invention.
Figure 3:
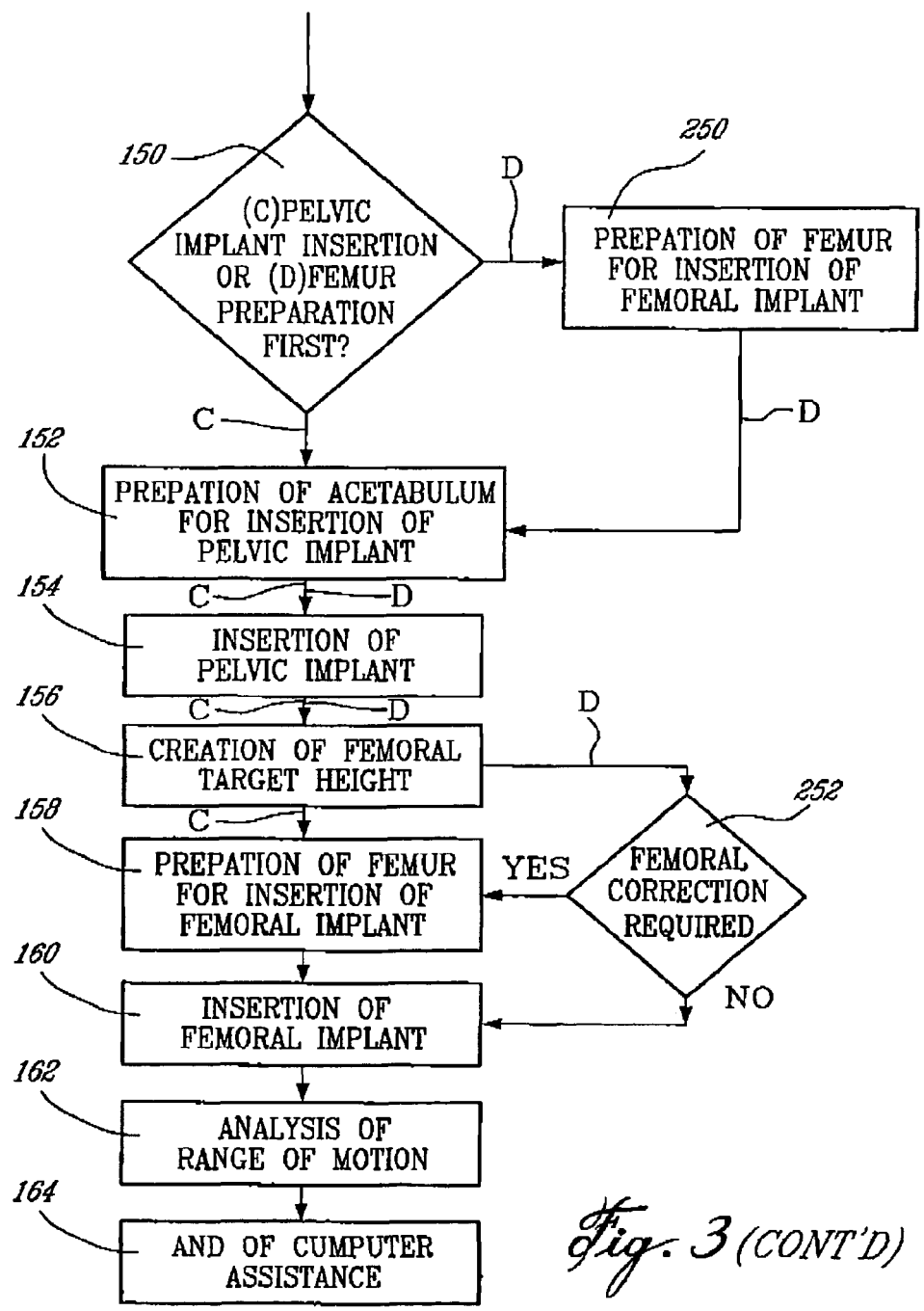

Referring to FIG. 3, a method for hip replacement surgery in accordance with the present invention is generally shown at 100. Although the method 100 is referred to in the singular, various choices of procedure will be given to the surgeon, as will be set forth in the forthcoming description, according to the preferences of the surgeon. A plurality of methods can be derived from the method 100 according to the decisions of the surgeon.

In Step 102, preparative steps for surgery are effected. Namely, general patient information can be entered into the CAS system 50 (FIG. 2) for opening a patient file. For instance, a general patient profile can be entered, consisting of the name, birth date, identification number, sex and the like, as well as more specific data pertaining to the surgery, such as leg length discrepancy (with the identification of the longer leg), if applicable. For instance, the leg length discrepancy is measured using X-rays of the hip joint. More precisely, the leg length discrepancy is measured from the vertical comparison between the lesser trochanters. These X-rays are typically taken during the diagnostic stages leading to surgery, so they are usually available for hip joint surgery. The calibration of the various surgical tools to be used is done. For instance, a calibration base and method, as set forth in International Publication No. WO 01/67979 A1 by Jutras et al., can be used for the calibration. Also, correspondence between the tracking of the tools 56 and the display on the CAS controller 52 can be verified in further calibration steps included in Step 102.

It is pointed out that the general patient information can be entered preoperatively. Moreover, the entering of the general patient information is straightforward such that the surgeon need not be involved. However, in order to minimize the preoperative procedures, all steps of method 100 can be performed at the beginning of the surgical session, during short time span preceding the surgery.

Surgery is initiated between Step 102 and subsequent Decision 104, by the surgeon exposing the hip joint. No computer assistance is required thereat.

In Decision 104, the surgeon is given the choice of proceeding either with (A) the dislocation of the femur from the pelvis, or with (B) the resection of the femoral head from the femur. Both (A) and (B) will lead to the obtainment of frames of reference for both the femur and the pelvis, as will be explained hereinafter, but both (A) and (B) have advantages over the other. For reference purposes, flow chart lines have been identified as (A) or (B) for the method 100 in FIG. 3, in accordance with the choice of the surgeon.

The dislocation of the femur from the pelvis (A) is preferred, as centers of rotation of the acetabulum 11 and the femoral head 21 (FIG. 1) will be digitized independently from one another. In (B) resecting the femoral head 21 from the femur 20 to then remove the femoral head 21 from the acetabulum 11, the femoral head 21 will not be exposed out of the acetabulum 11 until it is resected, whereby the center of rotation thereof cannot be digitized with respect to the rest of the femur 20. Therefore, a calculation based on an assumption will enable the calculation of a theoretical femoral center of rotation.

On the other hand, dislocation (A) of the femur 20 shows some level of difficulty, and involves risks such as fracture of the femur 20 (e.g., at the neck 22), and damage (e.g., hyperextension) to ligaments and muscle. Resection (B) of the femoral head 21 can be preferred by surgeons as a safer procedure.

Procedure (A) will initially be described in detail, followed by a description of procedure (B).

Referring to FIG. 1 (for bone parts reference) and FIG. 3, in Step 106, following the choice of (A) dislocating the femur 20 from the pelvis 10, the femoral head 21 is removed from the acetabulum 11. Therefore, both the acetabulum 11 and the femoral head 21 are exposed.

In Step 108, tracking references (included in the tools 56) are secured to the pelvis 10 and the femur 20. Therefore, both the pelvis 10 and the femur 20 can be tracked for position and orientation in space simultaneously as a function of their respective tracking references, by the CAS system 50 of FIG. 2. The tracking references will remain anchored to their respective bones throughout the computer-assisted steps of surgery. It is pointed out that Step 108 could have been performed prior to Step 106 in procedure (A), although it is preferred that the tracking references not interfere with the dislocation of the femur 20. The CAS system 50 must thus be adapted to track at least two tracking references simultaneously, and in real-time.

It is pointed out that the tracking reference may take the form of a marked point on one of the bone elements. For instance, a tracking reference, of the type being screwed to the bone element, can be secured to the pelvis 10 to be tracked for position and orientation, while the femur 20 is solely marked with a point (e.g., from a physical or visual marker). In order to relate the marked point on the femur 20 to the tracking reference on the pelvis 10, the marked point is registered when the pelvis 10 and the femur 20 are in a known and reproducible posture. Thereafter, to update the position and orientation information relating to the femur 20 during surgery, the known and reproducible posture is reproduced and the marked point is digitized with a registration pointer.

It is also contemplated to provide a portable tracking reference that is positionable on a bone element in a reproducible way. For instance, instead of having a single marked point, the femur 20 may be marked with three nonlinear points to be used to position the portable tracking reference thereon. With such a portable tracking reference, position and orientation information for the femur 20 can be obtained by positioning the portable tracking reference with respect to the three non-linear points. The portable tracking reference is advantageous in that no screw holes are performed in the bone element.

Nonetheless, the method 100 will be described with a tracking reference anchored to the femur 20 in accordance with a preferred embodiment of the present invention. Yet it is appreciated that the above described alternatives could be used instead of the anchored tracking reference of the femur 20.

Referring to FIGS. 1 to 3, in Step 110, digitization of a center of the femoral head 21 is performed. For instance, a registration pointer (from the tools 56) having its tip tracked in space is used to register points on the surface of the femoral head 21. Therefore, points of contact between the tip and a given surface can be registered as a function of the tracking reference (Step 108). As tracking references have been secured to the femur 20 and the pelvis 10 in Step 108, the points on the surface of the femoral head 21 are known as a function of the tracking of the respective tracking reference of the femur 20. The CAS controller 52 is equipped with software that will enable it to calculate the center of a sphere (i.e., the femoral head 21) from the collected points. Moreover, the center calculation software is adapted to perform a validation of the center calculation with the standard and maximum deviations. A rejection criterion for the validation of the center calculation can be recorded, for instance, during the setting of parameters in Step 102.

Although the above described Step 110 is preferred for obtaining a 3D model from which the femoral center of rotation will be calculated, other equivalent methods are contemplated for obtaining the femoral center of rotation. For instance, photogrammetric scans can be used to rapidly create 3D models, or preoperative computerized tomography images can be gathered, from which the femoral head geometry can be established.

The diameter of the sphere (i.e., of the femoral head 21) can be displayed, as such information can guide the surgeon in the choice of a femoral implant. The femoral center of rotation and the diameter of the femoral head 21 can be used to correct displays on the CAS controller 52. Although CT images can be shown on the display unit of the CAS controller 52, the method 100 is preferably free of CT images. Accordingly, general visual images of the pelvis 10 and of the femur 20 can be displayed for general reference, but these images can be scaled as a function of the center of rotation and diameters, calculated in Step 110 for the femur 20 in procedure (A), and to be calculated in Step 114 for the pelvis 10.

In Step 112, with the center of the femoral head 21 now identified in procedure (A) as a function of the tracking reference (Step 108), resection of the femoral head 21 is performed.

Referring to FIGS. 1 to 3, in Step 114, digitization of the acetabular center of rotation is performed, by taking reference points on the surface of the acetabulum 11, and using the center calculation software of the CAS controller 52, set forth in Step 110 to find the acetabular center of rotation. The acetabular center of rotation is therefore known as a function of the tracking reference on the pelvis 10. It is noted that in procedure (A) the digitization of the acetabular center of rotation (Step 114) is done independently from the digitization of the femoral center of rotation (Step 110).

Step 116 consists in the digitization of the acetabular and femoral coordinate systems, i.e., the acetabular and femoral frames of reference.

The acetabular coordinate system is digitized with the registration pointer. In a preferred embodiment of the invention, three points are taken on the pelvis 10 to create the acetabular coordinate system. Referring to FIG. 1, there is one point on the iliac crest 12 of the operated side, one point on the contra lateral iliac crest 13, and one point on one of the two pubic tubercles 14 of the pelvis 10. To be generally aligned, the points digitized on the iliac crests 12 and 13 are taken at the-outermost anterior point of the iliac crests 12 and 13. The points digitized on the iliac crests 12 and 13 are preferably taken directly on the soft tissue covering the bone pelvis on the iliac crests, as the soft tissue is relatively thin thereon. The point on the pubic tubercle 14 completes a first plane, the frontal plane. A second plane, the transverse plane, is perpendicular to the frontal plane and includes the points on the iliac crests. A third plane, the sagittal plane, is perpendicular to the frontal and transverse planes.

Supplemental information regarding the frontal plane can be obtained for various postures of a patient. For instance, trackable references can be used to gather information about sitting, standing and walking postures. This information can be used to adjust the orientation of the frontal plane, as these postures can provide information not available from the typical lying posture in which a patient is during surgery. This information can influence the anteversion positioning of the implants.

It is possible to obtain anteversion and/or inclination values of the acetabulum of the patient, to be used as a reference (e.g., comparison basis) later in the surgery. To do so, points are digitized (using a registration pointer from the tools 56) on the generally circular edge of the acetabulum 11 and a plane is defined from these points. A normal to this plane is projected onto the acetabular transverse plane (as defined in Step 116) to give an anteversion angle with the intersection of the acetabular frontal plane and transverse plane. The normal to this plane is projected onto the acetabular sagittal plane (as defined in Step 116) to give an inclination angle with a cranial-caudal axis (y) on the acetabular sagittal plane.

In a preferred embodiment of the present invention, the femoral coordinate system is digitized in Step 116 by providing five points of reference on the leg to the CAS controller 52, which is equipped with software that will create the femoral coordinate system. Referring to FIG. 1, a first point is taken on the tip of the greater trochanter 23 of the femur 20, and will be defined as a starting point of an anatomical axis of the femur 20. Thereafter, points are taken on the medial and lateral epicondyles 24 and 25 of the femur 20, respectively. A midpoint between the medial epicondyle and lateral epicondyle points, in alignment therewith, is defined as an endpoint of the anatomical axis of the femur. The fourth and fifth points are taken on the medial malleolus 31 of the tibia 30 and on the lateral malleolus 41 of the fibula 40, with the leg being bent at the knee. By having the leg bent at the knee, the tibia 30 stands on the posterior condyles 26 of the femur 20. Therefore, an assumption is made wherein an aligned midpoint of the medial and lateral malleoli points is said to define a plane (i.e., sagittal plane) with the anatomical axis, with an axis of the knee being normal to the sagittal plane. The frontal plane is perpendicular to the sagittal plane, with the anatomical axis lying therein. The transverse plane is perpendicular to the sagittal and frontal planes, and can be positioned at any height. With the anatomical axis and the midpoint of the malleolus region digitized, the femoral coordinate system, i.e., the femoral frame of reference, is complete. It is noted that it is not required to measure two points to obtain a midpoint of the malleolus region. As this latter point will be in the sagittal plane, the only requirement is that a point is taken at a midpoint of the malleolus region, and may thus be placed approximately by the operator.

It is pointed out that the projection values described herein (e.g., inclination, anteversion, etc.) are based on the acetabular and the femoral coordinate systems. As it is contemplated to use alternative methods of digitizing the acetabular and the femoral coordinate systems, in addition to the preferred methods of Step 116, the projection values would be related to the alternative acetabular and femoral coordinate system.

Now that the procedure (A) has been described, the procedure (B), involving the resection of the femur 20 without the dislocation thereof, will be described. It is pointed out that some of the steps described for procedure (A) are also performed in procedure (B), as readily seen in FIG. 3. Therefore, unless stated otherwise, corresponding steps will involve the same features and will not be described in detail for procedure (B). As shown in FIGS. 1 and 3, the first step of the surgical procedure following the decision to proceed with the resection (B) is Step 108, wherein tracking references are secured to the pelvis 10 and to the femur 20.

Referring to FIGS. 1 and 3, Step 200 consists in a registration of a relative position between the pelvis 10 and the femur 20, as a function of the tracking references on each. The leg is simply left in a straight position, and a relative position is acquired between tracking references secured to their respective bones.

In procedure (B), Step 112 of resecting the femoral head 21 from the femur follows Step 200. Accordingly, the acetabulum 11 of the pelvis 10 is exposed, and Step 114, consisting in the digitization of the acetabular center of rotation, follows.

As mentioned previously, the digitization of the acetabular center of rotation is as a function of the tracking reference secured to the pelvis 10.

Step 202 includes the calculation of the femoral center of rotation. In this calculation, an assumption is made that the acetabular center of rotation, calculated in the previous Step 114 in procedure (B), coincides with the femoral center of rotation. However, as the pelvis 10 and the femur 20 are separated due to the resection of the femoral head 21 in Step 112, the position of the femoral center of rotation is calculated as a function of the relative position between the pelvis 10 and the femur 20, obtained in Step 200.

Step 116 follows, with the digitization of acetabular and femoral coordinate systems, i.e., acetabular and femoral frames of reference.

Therefore, procedures (A) and (B) have now generally gathered the same data. At this point, Decision 150 follows, wherein the surgeon is given the choice of proceeding first with (C) the insertion of the pelvic implant, or with (D) the preparation of the femur for the insertion of the femoral implant.

Once more, procedures (C) and (D) will each have their respective advantages. Procedure (C) is the preferred embodiment and will most likely involve at least one fewer step. Some surgeons may prefer the procedure (D) as it involves work on the femur 20, which has just been resected to lose its femoral head 21 (Step 112).

Procedure (C) will initially be described, followed by a description of procedure (D).

Step 152 is the first step of procedure (C), and consists in the preparation of the acetabulum for insertion of the pelvic implant. Typically, the preparation of the acetabulum is performed by a reamer (from amongst the tools 56 of the CAS system 50). The previous acetabular center of rotation is known as a function of the tracking reference secured to the pelvis 10, as it was acquired in previous Step 114. Preferably, the reamer is tracked for position and orientation, such that an axis of actuation of the cup tool on the reamer is displayed on the CAS controller 52.

In Step 152, the diameter of the pelvic implant chosen by the surgeon will be used to display a position of the new acetabular center of rotation in comparison to the digitized acetabular center of rotation (Step 114). For instance, the distance between the centers of rotation can be displayed numerically (e.g., in mm) as a function of the acetabular coordinate system digitized in previous Step 116. Also, the anteversion and inclination of the actuation axis of the reamer, both as a function of the acetabular coordinate system, can be given numerically (e.g., in degrees) to guide the surgeon in the reaming. More precisely, the anteversion is calculated as the angle between an intersection of the acetabular frontal plane and transverse plane and the projection of the axis of the reamer on the acetabular transverse plane, and the inclination is the angle between the reamer axis and a cranial-caudal axis (y) on the sagittal plane of the acetabular coordinate system (Step 116).

Step 154 consists in the insertion of the pelvic implant in the acetabulum 11. A tracked impactor (from amongst the tools 56) is preferably used. As the pelvic implant size has been chosen, the diameter thereof and the known relation between the impactor and the pelvic implant is used with the tracking of the impactor to give the anteversion and the inclination of the pelvic implant. Also, the distances between the current and the digitized centers of rotation can be displayed. Therefore, the surgeon is guided during the use of the impactor so as to position the pelvic implant to a given position of the center of rotation thereof, and to a given orientation [with respect to anteversion and inclination (Step 152)] to provide a maximal range of motion and stability of the leg.

Although the pelvic implant is secured at this point to the pelvis 10, it is possible to adjust the position and orientation of the pelvic implant. Firstly, the tracked impactor may be reconnected to the pelvic implant to serve as a lever in manipulating the pelvic implant with the tracked impactor, allowing position and orientation information (e.g., anteversion and inclination) to be calculated from the tracking of the impactor. Alternatively, points on the circular edge of the pelvic implant may be digitized to define a plane, with the normal to this plane being used to calculate the anteversion and the inclination, as suggested previously to obtain this information for the acetabulum. This alternative approach is well suited for pelvic implants having screw holes for additional fixation, through which the implants can be altered in position and orientation.

Step 156 consists in the creation of a femoral target height. The target height is a desired position for the femoral center of rotation, and is calculated as follows:

$$(\text{target height}) = (\Delta_{PELVIC\ COR}) - (\text{initial } \Delta_{LL}),$$

where $(\Delta_{PELVIC\ COR})$ is the deviation of the implant center of rotation (i.e., Step 154) with respect to the digitized acetabular center of rotation (i.e., Step 114), in cranial-caudal (y) direction (with a cranial deviation having a positive value), and (initial $\Delta_{LL}$) is the initially acquired limb length discrepancy (Step 102).

Referring to FIGS. 1 and 3, Step 158 consists in the preparation of the femur 20 for the insertion of the femoral implant. More precisely, an axis of the intramedullary canal 27 is digitized as a function of the tracking reference secured to the femur 20 by relating points in the canal 27. The intramedullary canal 27 is exposed by the resection of the femoral head 21 performed in Step 112. In an embodiment of the present invention, the points in the canal 27 are digitized by the insertion and tracking of a pointer (from amongst the tools 56) in the canal 27, to various depths. It is also contemplated to use a tool, such as an awl, that is trackable in space for position and orientation, and whose axis is known with respect to the tracking. The awl can be inserted in the intramedullary canal to a depth wherein the inner diameter of the intramedullary canal is generally equivalent to the awl. At such a depth, the awl can be considered to be generally centered in the intramedullary canal, whereby the axis of the awl can be registered as being the axis of the intramedullary canal.

Figure 4:
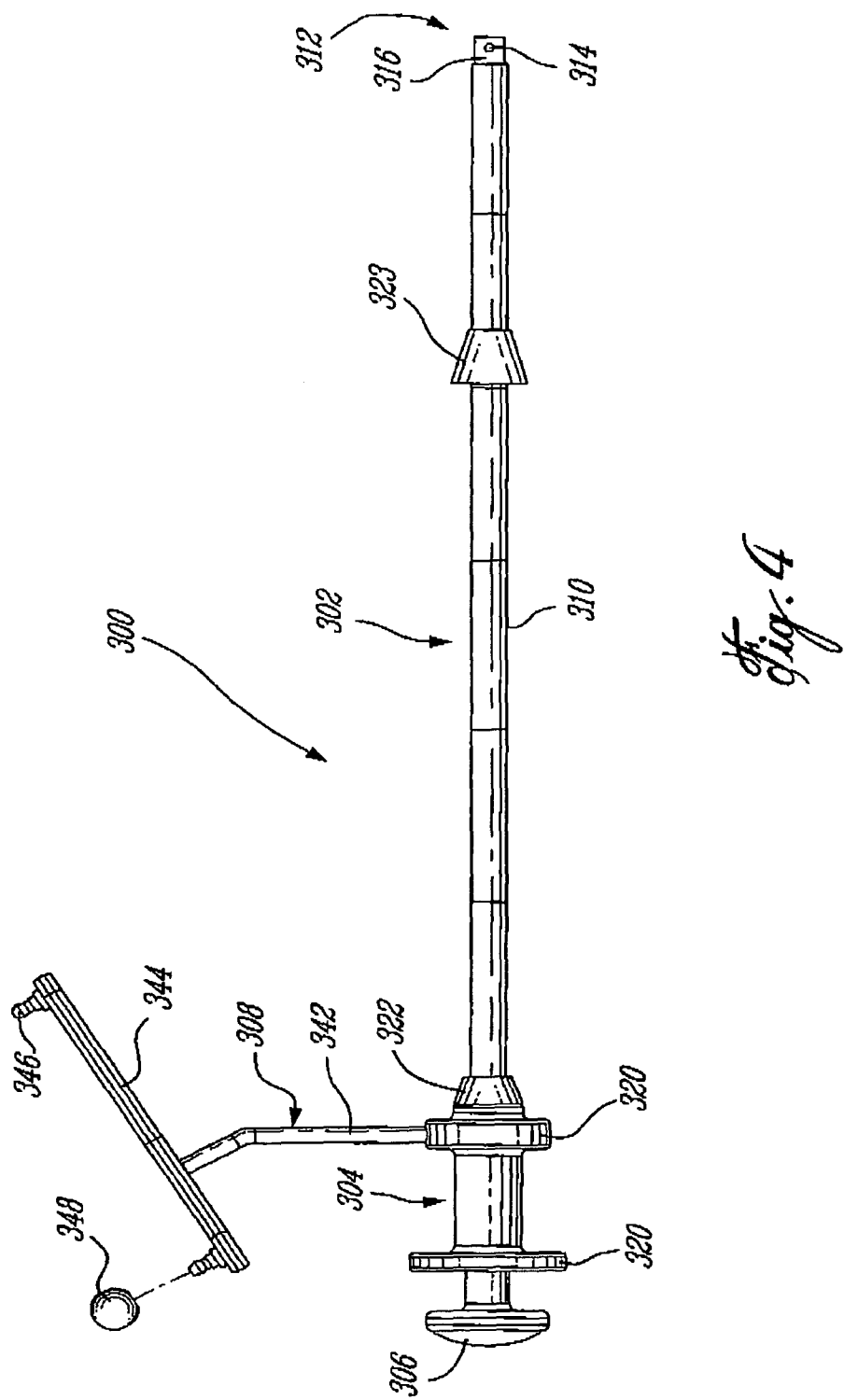
FIG. 4 is a front elevation view of a canal digitizer in accordance with the present invention.

Referring to FIG. 4, a canal digitizer in accordance with a preferred embodiment of the present invention is generally shown at 300. The canal digitizer 300 can be used to accurately position a tip thereof in the center of the intramedullary canal 27, and hence an axis centered in the canal 27 can be digitized. The canal digitizer 300 will be described in further detail hereinafter.

Step 158 also includes the rasping of the intramedullary canal 27 in view of the insertion of the femoral implant therein. The rasp is part of the tools 56 of the CAS system 50, and is therefore tracked for position and orientation. The tooling portion of the rasp, which will alter the intramedullary canal 27, and the femoral implant both have a predetermined geometry. It is preferred to have rasps each having a tooling end with a generally similar geometry to the bone-engaging portion of the femoral implants. Moreover, the rasps can be provided in different sizes, with an equivalent femoral implant for each size of rasp. Therefore, the tracking of the rasp for position and orientation relative to the femoral coordinate system during alteration of the canal is used to calculate the current position and orientation of the femoral implant. A plurality of guiding parameters are displayed to the surgeon to quantify the current position and orientation of the femoral implant, and are listed below.

The anteversion of the femoral implant as calculated from the tracked rasp can be displayed numerically (e.g., in degrees) based on the femoral coordinate system calculated in Step 116. It is represented by the angle between the intersection of the frontal plane and the transverse plane and a projection of the neck axis (anticipated for the femoral implant) onto the transverse plane (Step 116).

Another guiding parameter to be provided to the surgeon is the varus/valgus angle of the femoral implant, which is equivalent to the varus/valgus angle of the tracked rasp. The angle is measured between the projection of t he intramedullary canal axis and the projection of the longitudinal rasp axis onto the femoral frontal plane (Step 116), and is displayed to the surgeon in degrees.

Another guiding parameter to be provided to the surgeon is the distance between the previous femoral center of rotation [i.e., digitized in Step 106 for the dislocation procedure (A), or calculated in Step 202 for the resection procedure (B)] and the current femoral center of rotation. The current femoral center of rotation is calculated as a function of the femoral implant geometry (e.g., the ball head size) and the tracking of the rasp. The distance can be given in X, Y and Z values (e.g., in mm) according to the femoral coordinate system. (Step 116).

Another guiding parameter to be provided to the surgeon is the current leg length discrepancy. The current leg length discrepancy, (current $\Delta_{LL}$), is calculated as follows:

$$(\text{current } \Delta_{LL}) = (\text{initial } \Delta_{LL}) - (\Delta_{PELVIC\ COR}) + (\Delta_{FEMUR\ COR}),$$

where ($\Delta_{FEMUR\ COR}$) is the Y value calculated above in Step 158, and where ($\Delta_{PELVIC\ COR}$) and (initial $\Delta_{LL}$) have been calculated in Step 156. The current leg length discrepancy can be displayed by the CAS system 50 as an overall leg length, or as a relative value between leg lengths, with the value 0 representing legs of equal length.

Another guiding parameter is the offset of the femoral implant. The offset is the distance between the acetabular center of rotation and the axis of the implant (i.e., the anatomical axis of the femur as defined previously) on the transverse plane, and is thus directly related to the size of the femoral implant. It is pointed out that a type of femoral implant contemplated for the above described method 100 can be provided in various sizes, and a size of femoral implant can have various femoral centers of rotation along the neck of the implant. A proper identification of the size of the femoral implant must therefore be provided as it will have an effect on both the offset and the limb length.

It may also be desired to display the sum of the measured femoral and acetabular distances in the X-axis.

Once the surgeon is satisfied with the rasped intramedullary canal 27 in procedure (C), the femoral implant is inserted. Step 160 consists in the insertion of the femoral implant in the intramedullary canal 27. It is anticipated that the femoral implant will be positioned and orientated substantially as calculated from the tracking of the tool 56 that has previously altered the intramedullary canal. However, it is also contemplated to track the femoral implant for position and orientation with a position of the center of rotation of the implant being calculable by the CAS controller 52 as a function of the tracking of the femoral implant. Such a step would ensure a precise position of the implant. The CAS controller 52 can change its display of the femur 20 upon the insertion of the femoral implant, or of the pelvis 10 upon the insertion of the pelvic implant (Step 154).

Step 162 consists in the analysis of the range of motion of the hip joint. The range of motion can be assessed by the following parameters: the angles of flexion/extension, of adduction/abduction, and the internal/external rotation of the leg. These angles are measured based on both coordinate systems digitized in Step 116, and the minimal and maximal angle values can be recorded as part of the patient profile.

Step 164 signals the end of the computer assistance to the hip replacement surgery.

Now that procedure (C) has been described in detail, procedure (D), involving the femur preparation prior to the pelvic implant insertion, will now be described. In procedure (D), Step 250 follows Decision 150, and consists in the same operations effected in Step 158. Namely, the femur 20 is prepared for the insertion of the femoral implant. However, an assumption is made that the actual pelvic implant center of rotation will be coincident with the digitized acetabulum center of rotation (Step 114). The digitized acetabulum center of rotation will thus be used in providing the various guiding parameters to the surgeon.

Following Step 250, procedure (D) comprises Steps 152, 154 and 156, as performed in procedure (C). It is pointed out that in Step 154, the actual pelvic implant center of rotation is obtained.

In Decision 252, a comparison is made between the actual pelvic implant center of rotation and the digitized acetabulum center of rotation, that has been used for the preparation of the femur in Step 250. If there is a difference between these values, femoral correction may be required, as shown in Step 158. Otherwise, the femoral implant can be inserted in the femur.

Thereafter, Steps 162 and 164 follow to end procedure (D).

Now that the method 100 has been described in detail, the CAS system 50 will be described in accordance with the preferred embodiment of the present invention.

Referring to FIG. 2, an operator (e.g., surgeon) is illustrated at S and is guided in performing surgery by the CAS system 50. More specifically, the operator S interacts with the controller 52 of the CAS system 50 using the user interfaces of the controller 52 (e.g., mouse, display unit, keyboard, sound emitter). As shown in FIG. 2, the controller 52 will provide guiding information on the method 100 to the operator S throughout CAS. The guiding information is for instance retrieved by the controller 52 from the database 58, and will guide the operator S in handling the tools 56.

The tools 56 are each trackable in space for position and orientation by the sensing apparatus 54, such that a position and/or orientation of given components thereof are calculable. As a general basic requirement, the tools 56 include the reference tools, such as the trackable references securable to the bones (Step 108), for the creation of frames of reference of the bones. Another one of the required tools 56 is a registration tool that will enable to gather surface information about the bones (e.g., Steps 110, 114, 116, etc.). As mentioned previously, the registration tool can be a registration pointer, a tracked photogrammetric sensor, or the like. Finally, a bone altering tool is included in the required tools 56, such as a reamer and a rasp, for which uses have been described previously in Steps 152 and 158, respectively. Also, the tools 56 include the pelvic (impactor) and the femoral implant, that can be tracked for position and orientation, to guide the operator during the insertion. It is pointed out that information relating to the tools (e.g., geometry, position of tip) is either known by the controller 52 (or retrievable from the database 58) or determinable using various steps of calibration.

The sensing apparatus 54 is connected to the controller 52, and transfers position and orientation tracking to the controller 52. The position and orientation trackings are used by the controller 52 to calculate parameters pertaining to the CAS. More precisely, the position and orientation trackings of the reference tool and registration tool are used to create frames of reference of the pelvis and the femur, as described in Steps 110, 114 and 116. As shown in FIG. 2, the frame of reference information is provided to the operator S, for instance using the display unit of the controller 52.

For the pelvic implant, an initial center of rotation is calculated with respect to the frame of reference, as described in Step 114. The acetabular center of rotation will be used with the pelvic frame of reference as references for the alteration of the acetabulum in view of the insertion of the pelvic implant therein. A desired femoral implant position is calculated by the controller 52 in accordance with the Step 156, and will be used as a reference for the alteration of the intramedullary canal in view of the insertion of the femoral implant therein. The database 58 stores information that is retrieved by the controller 52 to make the calculation.

The current pelvic and femoral implant positions and orientations are calculated as a function of the position and orientation tracking of the bone altering tools, and of the geometry of the respective implants. This is performed in accordance with Steps 154 and 158/252 of the method 100. Once more, the controller 52 uses the output of the sensor apparatus 54 and information stored in the database 58 for the calculations, that will be displayed for guiding the operator S.

The CAS system 50 can operate with active or passive tracking. In a preferred embodiment of the present invention, the sensor apparatus 54 is a NDI Polaris® optical tracking apparatus, with appropriate operating software in the controller 52. With the Polaris® optical tracking apparatus, passive detectable devices, such as retro-reflective spheres, are used in patterns to be tracked in space for position and orientation. Each one of the tools 56 that requires to be tracked has an own detectable pattern.

The CAS system 50 must guide the surgeon throughout the method 100, and relevant information is displayed to ensure the surgeon follows the proper Steps of operation. For instance, when leg length discrepancy values are given, the cranial-caudal convention can be displayed to explain the reading obtained. Animations can be initiated automatically to guide the surgeon, for example, in taking reference points on the various bones, such that the reference points are taken in a given order, or at the right locations.

Referring to FIGS. 4, 5A and 5B, the canal digitizer 300 is shown having an elongated shaft 302, a handle portion 304, a piston 306, a detectable device base 308, and a centering mechanism 309.

The shaft 302 is hollow, and has an outer surface 310 and a free open end 312. The shaft 302 is graduated such that when the digitizer 300 is inserted in a canal, the tool handler has an indication of the depth of insertion of the digitizer 300. As shown in FIG. 5A, a splitter 314 is provided at the free open end 312, and is held between a pair of extensions 316.

The handle portion 304 has a pair of radial flanges 320. The detectable device base 308 projects outwardly from a distal one of the radial flanges 320. The proximal flange 320 is adjacent to the piston 306, and is used as leverage by the tool handler to push the piston 306 inwardly. A flared tip 322 is adjacent to the distal flange 320, and will enable the digitizer 300 to be centered when abutting against walls of a canal, if the elongated shaft 302 is completely inserted in the canal.

The handle portion 304 also defines an inner cavity 324, having a guiding channel 325 adjacent to the proximal flange 320, for a purpose to be described hereinafter.

As shown in FIG. 4, a flared adapter 323 can be optionally provided in sliding engagement on the shaft 302. The flared adapter 323 serves the same purpose as the flared tip 322 of the handle portion 304, but is displaceable on the shaft 302 so as be used at various depths of insertion of the shaft 302 in the canal.

Figures 6, 7:
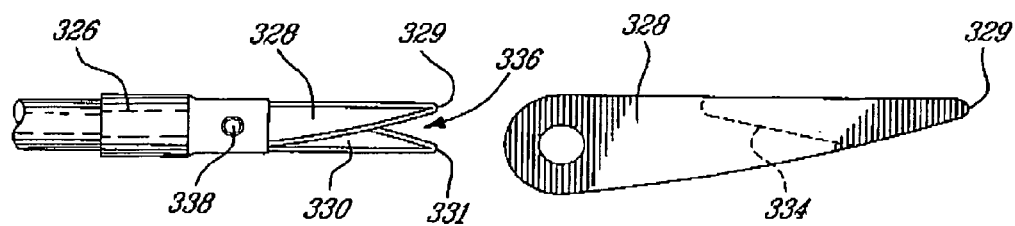
FIG. 6 is a front elevation view of fingers of the canal digitizer.
FIG. 7 is a front elevation view of one of the fingers having a stopper.

The centering mechanism 309 has a slender rod 326, concentrically disposed in the shaft 302. The rod 326 is connected to the piston 306 at a proximal end thereof, and has a pair of fingers, 328 and 330, pivotally mounted thereto at a distal end thereof, as best seen in FIG. 6. Returning to FIGS. 5A and 5B, a spring 332 surrounds a proximal portion of the rod 326, and interacts with a surface of the inner cavity 324 of the handle portion 304 such that the rod 326 is biased in the proximal direction, i.e., the piston 306 is held away from the handle portion 304. Accordingly, when the piston 304 is pushed in by the tool handler, the rod 326 moves in the distal direction, but retracts back proximally upon release of the piston 306. The spring 332 is fixed at a proximal end thereof to the piston 306, for instance, by welding therebetween.

The piston 306 has a pin 327 at a distal end thereof. The pin 327 cooperatively engages into the guiding channel 325 of the cavity 324 of the handle portion 304. Accordingly, the assembly of the piston 306/centering mechanism 309 can be readily separated from the shaft 302/handle portion 304 assembly by guiding the former from the latter until the pin 327 is out of the guiding channel 325. The guiding channel 325 has an elbow portion 325' (FIG. 5B) and a straight portion 325", such that once the pin 327 is past the elbow portion 325' (FIG. 5B) in the cavity 324, the piston 306/centering mechanism 309 assembly is captive and free to translate in the straight portion 325", being held captive with respect to the handle portion 304. This assembly is preferred to facilitate the sterilization of the inner cavity 324 and of the interior of the shaft 302.

Figure 8:
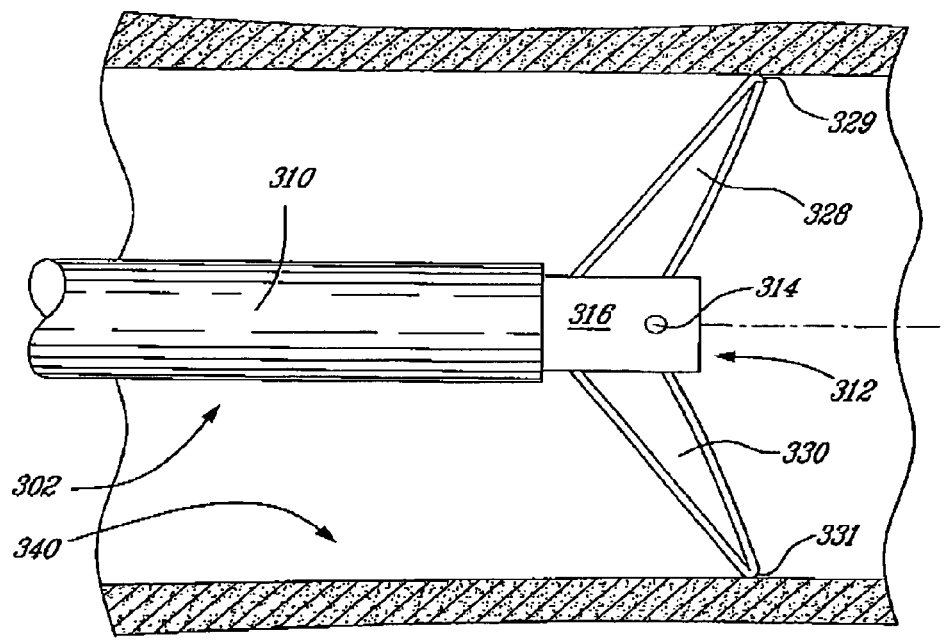
FIG. 8 is a front elevation view of the fingers of the canal digitizer centering the canal digitizer.

Referring to FIGS. 6 to 8, the fingers 328 and 330, at the distal end of the rod 326, are kept with their respective tips 329 and 331 separated from one another by a stopper 334 protruding from the finger 328. Therefore, the fingers 328 and 330 define a slot 336. The fingers 328 and 330 are held by pivot 338. The tips 329 and 331 are both at a same distance from the pivot 338.

When the piston 306 is pushed inwardly, the rod 326 moves towards the free open end 312 of the shaft 302, such that the splitter 314 engages with the slot 336. In doing so, the fingers 328 and 330 are guided away from one another, as best seen in FIG. 8. If the digitizer 300 is in a canal, as shown at 340 in FIG. 8, the fingers 328 and 330 will center the digitizer 300 in the canal. Other configurations are possible. For instance, a pivotless solution can also be imagined where fingers 328 and 330 would be two blades protruding from a same solid and the flexion of the material would split the blades apart when engaged on the splitter 314. It has also been thought to equip the elongated shaft 302 with an inflatable end that will be self-centered in the intramedullary canal upon being inflated.

The rod 326 has a given length, such that the fingers 328 and 330 at an end thereof do not interfere with the splitter 314 when the assembly of the piston 306/centering mechanism 309 (including the rod 326) is screwingly inserted in the shaft 302/handle portion 304. Such interference would prevent the pin 327 from going past the elbow portion 325' of the guiding channel 325 in the inner cavity 324. Another possible configuration is to provide an axial rotational degree of freedom between the piston 306 and the rod 326. Therefore, an engagement of the fingers 328 and 330 with the splitter 314 would not prevent the engagement of the pin 327 of the piston 306 in the guiding channel 325 of the inner cavity 324. This can be achieved by providing an annular groove 339 on an end of the rod 326, and corresponding engagement pins 341 between the grooves 339 and the piston 306.

The digitizer 300 is used with a tracking system, such as CAS system 50 (FIG. 2). As CAS system 50 is preferably equipped with an optical tracking system, the digitizer 50 is shown having the detectable device base 308 consisting of a support for detectable devices. More precisely, the detectable device base 308 has an arm 342 with a support plate 344 at a free end thereof. Snap-fit fingers 346 are provided for receiving detectable devices in snap-fit engagement therewith. For instance, the detectable devices can be retro-reflective detectable spheres, one of which is shown at 348 in FIG. 4 on the verge of being snap-fitted to one of the fingers 346. It is obvious that the digitizer 300 may also be equipped with an active detectable device, provided that the tracking system is configured therefor.

The tracking system used with the digitizer 300 must know the relation between the detectable device on the base 308 and the tip of the shaft 302. The relation can be determined in calibration base (as explained previously for the tools 56 of FIG. 2). Accordingly, when the digitizer 300 is stabilized in the canal, the position and orientation of the detectable device can be registered, and a center point of the canal can be calculated thereafter, where the tip of the shaft 302 is located.

We claim:

1. A method of doing surgical treatment with a tracking system in computer-assisted surgery for guiding an operator in inserting a femoral implant of a hip joint implant in a femur as a function of a limb length and orientation of the femoral implant, comprising:
    obtaining a frame of reference of the femur, the frame of reference being trackable in space;
    obtaining a digital model of a geometry of a femoral implant, and a digital model of a geometry of a tooling end of a rasp;
    calculating a desired implant insertion for the femoral implant with respect to the frame of reference of the femur, as a function of the limb length;
    calculating alterations being made to a femur with a real-time tracking of the rasp altering the femur for receiving the femoral implant and with the digital model of the geometry of the tooling end of the rasp; and
    determining a current implant insertion with respect to the desired implant insertion, the current implant insertion being calculated as a function of the digital model of the femoral implant and the calculated alterations.

2. The method according to claim 1, wherein determining the current implant insertion includes determining at least one of the varus/valgus angle of the femoral implant, the anteversion of the femoral implant, and an offset of the femoral implant.

3. The method according to claim 2, wherein the varus/valgus angle of the femoral implant is calculated as a function of an axis of the intramedullary canal in relation to an axis of the femoral implant with respect to the frame of reference, and obtaining the axis of the intramedullary canal is performed by:
    performing an opening in the femur;
    providing a tool trackable in space, said tool having a leading end thereof being insertable in a determined way with respect to a surface of the intramedullary canal; and
    obtaining the axis of the intramedullary canal with respect to the frame of reference by calculating and relating reference points in the intramedullary canal by inserting the leading end of the tool at given depths in the intramedullary canal and calculating a reference point of the intramedullary canal for each said given depths as a function of a tracking of said tool having the leading end inserted in said determined way.

4. The method according to claim 1, wherein determining the current implant insertion is repeated following a change in the desired implant insertion caused by a change in an acetabular center of rotation.

5. The method according to claim 1, further comprising guiding the operator in inserting the femoral implant in the intramedullary canal by tracking the femoral implant during the insertion.

6. The method according to claim 1, wherein obtaining the frame of reference of the femur is intraoperative.

7. The method according to claim 6, wherein the frame of reference of the femur includes a center of the femoral head, and obtaining the center of the femoral head is performed by:
    positioning a reference system trackable in space onto the femur;
    dislocating the femur from the pelvis;
    creating a digital model of a surface of the femoral head as a function of the reference system; and
    calculating a center of the femoral head as a function of the digital model of the surface of the femoral head.

8. The method according to claim 7, wherein the frame of reference further includes femoral sagittal, frontal and transverse planes, and obtaining the planes is performed by:
    registering a sagittal plane with respect to said reference system by digitizing an anatomical axis of the femur, a midpoint of the epicondyles and a midpoint of a tibia corresponding to the femur, the anatomical axis and a midpoint of the malleoli lying in the sagittal plane;
    registering a frontal plane with respect to said reference system, with the frontal plane being perpendicular to the sagittal plane and incorporating the anatomical axis; and
    registering a transverse plane with respect to said reference system, with the transverse plane being perpendicular to the sagittal plane and the frontal plane.

9. The method according to claim 6, wherein the frame of reference of the femur includes a center of the femoral head, and obtaining the center of the femoral head is performed by:
    positioning reference systems trackable in space onto the femur and onto a corresponding pelvis;
    registering a relative tracking value between said reference systems;
    separating the femur from the pelvis to expose an acetabulum of the pelvis;
    creating a digital model of a surface of the acetabulum as a function of the reference system on the pelvis;
    calculating a center of rotation of the acetabulum as a function of the digital model of the surface of the acetabulum; and
    calculating a center of rotation of the femoral head as a function of said relative tracking value between said reference systems, assuming that the center of rotation of the acetabulum is coincident with the center of rotation of the femoral head.

10. The method according to claim 9, wherein the frame of reference further includes femoral sagittal, frontal and transverse planes, and obtaining the planes is performed by:
    registering a sagittal plane with respect to said reference system on the femur by digitizing an anatomical axis of the femur, a midpoint of the epicondyles and a midpoint of a tibia corresponding to the femur, the anatomical axis and a midpoint of the malleoli lying in the sagittal plane;

registering a frontal plane with respect to said reference system on the femur, with the frontal plane being perpendicular to the sagittal plane and incorporating the anatomical axis; and registering a transverse plane with respect to said reference system on the femur, with the transverse plane being perpendicular to the sagittal plane and the frontal plane.

\* \* \* \* \*